(12) United States Patent
Krivoruchko

(10) Patent No.: US 7,309,353 B2
(45) Date of Patent: Dec. 18, 2007

(54) USE OF PLATINUM GROUP METALS IN VASCULAR DEVICES AND METHOD OF TEXTURING PLATINUM GROUP METALS

(75) Inventor: Mike Krivoruchko, Forestville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 323 days.

(21) Appl. No.: 11/118,080

(22) Filed: Apr. 29, 2005

(65) Prior Publication Data

US 2006/0247758 A1 Nov. 2, 2006

(51) Int. Cl.
*A61F 2/06* (2006.01)
*A61L 33/00* (2006.01)

(52) U.S. Cl. .................. 623/1.46; 75/633; 75/744; 427/2.1

(58) Field of Classification Search ...... 623/1.15–1.46; 75/633, 744; 427/2.1
See application file for complete search history.

(56) References Cited

U.S. PATENT DOCUMENTS

| | | | |
|---|---|---|---|
| 5,800,511 A | 9/1998 | Mayer et al. | |
| 6,010,445 A * | 1/2000 | Armini et al. | 600/3 |
| 6,152,869 A | 11/2000 | Park et al. | |
| 6,340,368 B1 | 1/2002 | Verbeck | |
| 6,399,886 B1 * | 6/2002 | Avellanet | 174/128.1 |
| 2004/0025986 A1 * | 2/2004 | Perry et al. | 148/577 |
| 2004/0110738 A1 * | 6/2004 | Gillis et al. | 514/184 |
| 2005/0066774 A1 * | 3/2005 | Asano et al. | 75/741 |
| 2005/0131522 A1 * | 6/2005 | Stinson et al. | 623/1.15 |
| 2006/0276875 A1 * | 12/2006 | Stinson et al. | 623/1.15 |
| 2007/0067009 A1 * | 3/2007 | Gandhi et al. | 623/1.11 |

FOREIGN PATENT DOCUMENTS

| | | |
|---|---|---|
| GB | 720025 | 12/1954 |
| GB | 1134492 | 11/1968 |
| JP | 01119595 | 5/1989 |
| JP | 2005287568 | 10/2005 |
| WO | WO 2005/044361 | 5/2005 |

* cited by examiner

*Primary Examiner*—Suzette Gherbi

(57) ABSTRACT

A method of texturing polycrystalline iridium includes the steps of cold/warm working of the polycrystalline iridium at equal to or below its re-crystallization temperature to break up the polycrystalline structure such that the orientation favors one direction (i.e. the <110> direction), and re-crystallizing the iridium such that a majority of grains are aligned in the preferred direction. The textured polycrystalline material is then used in vascular devices such as stents.

11 Claims, 2 Drawing Sheets

USE OF PLATINUM GROUP METALS IN VASCULAR DEVICES AND METHOD OF TEXTURING PLATINUM GROUP METALS

BACKGROUND OF THE INVENTION

1. Field of the Invention

The present invention relates to vascular devices. More specifically, the invention relates to the use of platinum group metals, in particular, iridium, in vascular devices.

2. Related Art

A wide range of medical treatments have been previously developed using "endoluminal prostheses," which terms are herein intended to mean medical devices which are adapted for temporary or permanent implantation within a body lumen, including both naturally occurring or artificially made lumens. Examples of lumens in which endoluminal prostheses may be implanted include, without limitation: arteries, such as those located within the coronary, mesentery, peripheral, or cerebral vasculature; veins; gastrointestinal tract; biliary tract; urethra; trachea; hepatic shunts; and fallopian tubes.

Various types of endoluminal prostheses have also been developed, each providing a uniquely beneficial structure to modify the mechanics of the targeted lumen wall. For example, stent prostheses have been previously disclosed for implantation within body lumens. Various stent designs have been previously disclosed for providing artificial radial support to the wall tissue, which forms the various lumens within the body, and often more specifically within the blood vessels of the body.

Cardiovascular disease, including atherosclerosis, is the leading cause of death in the U.S. The medical community has developed a number of methods and devices for treating coronary heart disease, some of which are specifically designed to treat the complications resulting from atherosclerosis and other forms of coronary arterial narrowing.

One method for treating atherosclerosis and other forms of coronary narrowing is percutaneous transluminal coronary angioplasty, commonly referred to as "angioplasty," "PTA" or "PTCA". The objective in angioplasty is to enlarge the lumen of the affected coronary artery by radial hydraulic expansion. The procedure is accomplished by inflating a balloon catheter within the narrowed lumen of the coronary artery. In some instances the vessel chronically restenoses, or acutely closes down, negating the positive effects of the angioplasty procedure.

To provide radial support to the treated vessel in order to prolong the positive effects of PTCA, a stent may be implanted in conjunction with the procedure. Effectively, the stent overcomes the natural tendency of the vessel walls of some patients to close back down, thereby maintaining a more normal flow of blood through that vessel than would be possible if the stent were not in place. Under this procedure, the stent may be collapsed to an insertion diameter and inserted into a body lumen at a site remote from the diseased vessel. The stent may then be delivered to the desired site of treatment within the affected lumen and deployed to its desired diameter for treatment.

Access to a treatment site is most often reached from the femoral artery. A flexible guiding catheter is inserted through a sheath into the femoral artery. The guiding catheter is advanced through the femoral artery into the iliac artery and into the ascending aorta. Further advancement of the flexible catheter involves the negotiation of an approximately 180 degree turn through the aortic arch to allow the guiding catheter to descend into the aortic cusp where entry may be gained to either the left or the right coronary artery, as desired. Because the procedure requires insertion of the stent at a site remote from the site of treatment, the device must be guided through the potentially tortuous conduit of the body lumen to the treatment site. Therefore, the stent must be capable of being reduced to a small insertion diameter and must be very flexible.

Stents are typically constructed from metal alloys that include any of stainless steel, nickel-titanium (NiTi or nitinol), cobalt-chromium (MP35N), platinum, platinum-iridium, and other suitable metals. Iridium in its pure form (i.e., not as part of an alloy) is generally not considered a good material for vascular devices such as stents because it is relatively brittle (not ductile) with poor elongation in its polycrystalline form. Stents and other vascular devices need to be flexible in order to navigate the tortuous vascular passages to reach the implantation site. Further, a stent must undergo significant plastic deformation when being expanded into its deployed state; this requires stent materials to have good elongation/ductility.

Despite its drawbacks, iridium has characteristics that would be beneficial in vascular devices, such as excellent corrosion resistance, high strength, high modulus, a rapid work-hardening rate, and excellent biocompatibility. Due to its relatively high atomic weight (77), iridium also exhibits high radiopacity, such that a vascular device such as a stent can be made thinner than a comparable stent made from stainless steel, yet exhibit equivalent strength and radiopacity. Because of its high modulus of Iridium, a vascular device can be designed with higher radial strength and less recoil than comparable device made of stainless steel or cobalt chromium such as, MP35N, or L605.

BRIEF SUMMARY OF THE INVENTION

The present invention is a method for processing polycrystalline iridium such that its room temperature ductility is greater than 10%.

In one embodiment, polycrystalline iridium is textured such that the crystallographic orientation of the grains are favorably aligned with the <110> tensile axis. In order to achieve this favorable alignment in polycrystalline material, a "fibrous" texture is created by significant cold/warm working of the material at below its re-crystallization temperature. Cold/warm working of the material needs to be such that the orientation of rolling favors alignment in the <110> direction. Subsequent recrystallization, if needed, needs to be controlled such that a majority of grains are aligned in one direction. This can be achieved by controlling the amount and direction of strain energy in the material.

Another method that can result in favorable orientation is to inhibit the re-crystallization of non-preferred oriented grains by the use of specific, lattice matched second phase particles. These particle act as nucleation sites or templates for orientation controlled re-crystallization or nucleation.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art based on the teachings contained herein.

BRIEF DESCRIPTION OF THE DRAWINGS

These and other features, aspects and advantages of the present invention will become better understood with reference to the following description, appended claims, and accompanying drawings.

DETAILED DESCRIPTION OF THE INVENTION

The present invention is now described with reference to the figures where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention.

Figure 1:
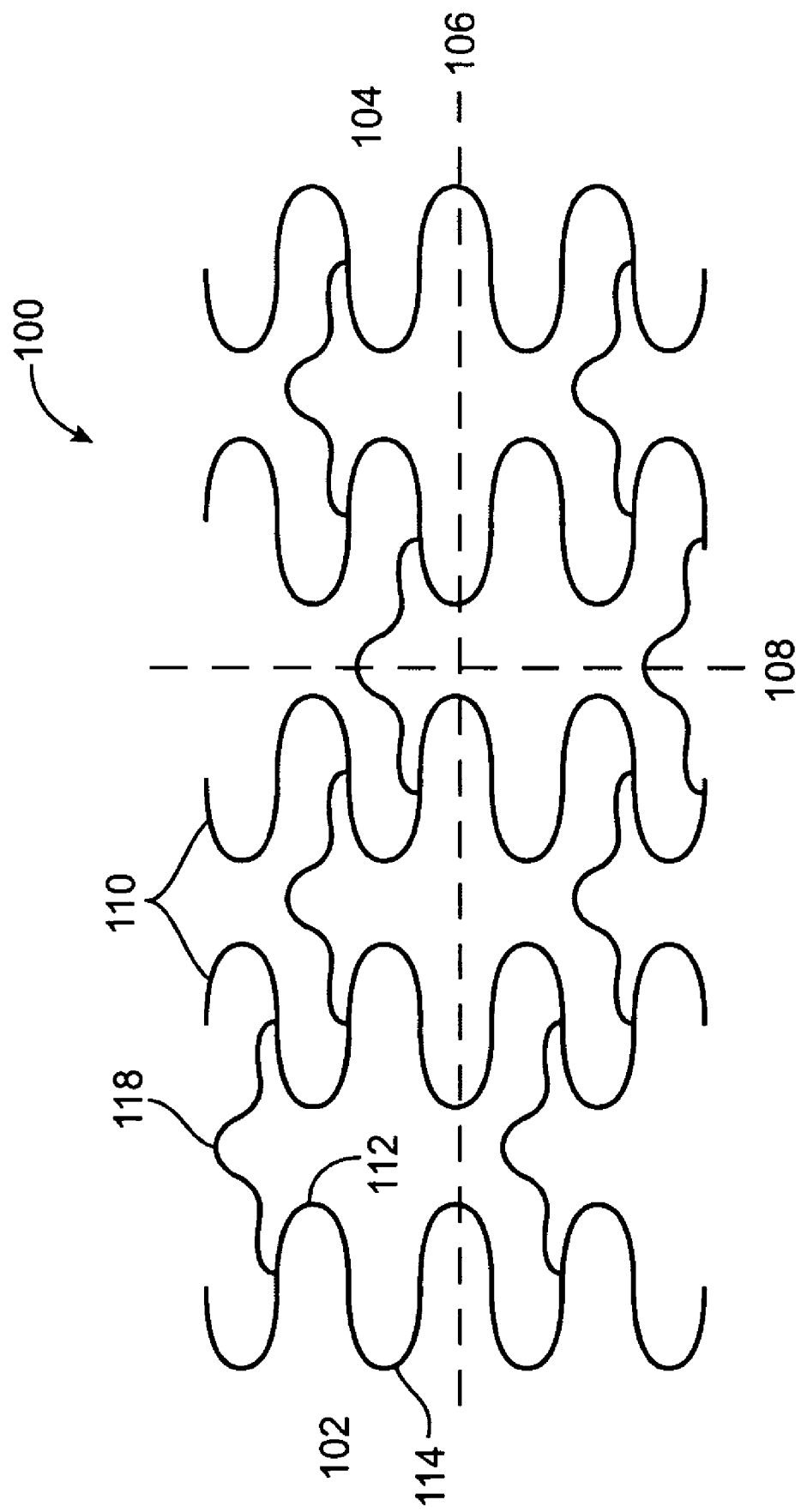
FIG. 1 is a top view of a stent of the present invention, which has been cut and laid open for illustrative purposes.

FIG. 1 shows a top view of an embodiment of a stent 100 according to the present invention, which has been cut and laid open for illustrative purposes. In its unaltered state, stent 100 is generally hollow and cylindrical in shape (not shown). Stent 100 has a proximal end 102 and a distal end 104. Additionally, stent 100 has a longitudinal axis 106 and a transverse axis 108.

Stent 100 comprises a plurality of circumferential rings 110. The circumferential rings are longitudinally spaced apart along longitudinal axis 106. The circumferential rings 110 are in the shape, for example, of a sinusoid. Each circumferential ring 110 comprises a plurality of peaks 112 and valleys 114. The distal end of the sinusoid has been arbitrarily labeled a peak and the proximal end of the sinusoid has been arbitrarily labeled a valley. It would be understood by one of ordinary skill in the art that peaks 112 and valleys 114 have been labeled for illustrative purposes and ease of understanding and that the terms may be switched. Further, although illustrated generally as sinusoidally shaped, it would be understood by one of ordinary skill in the art that other shapes can be used.

Figure 2:
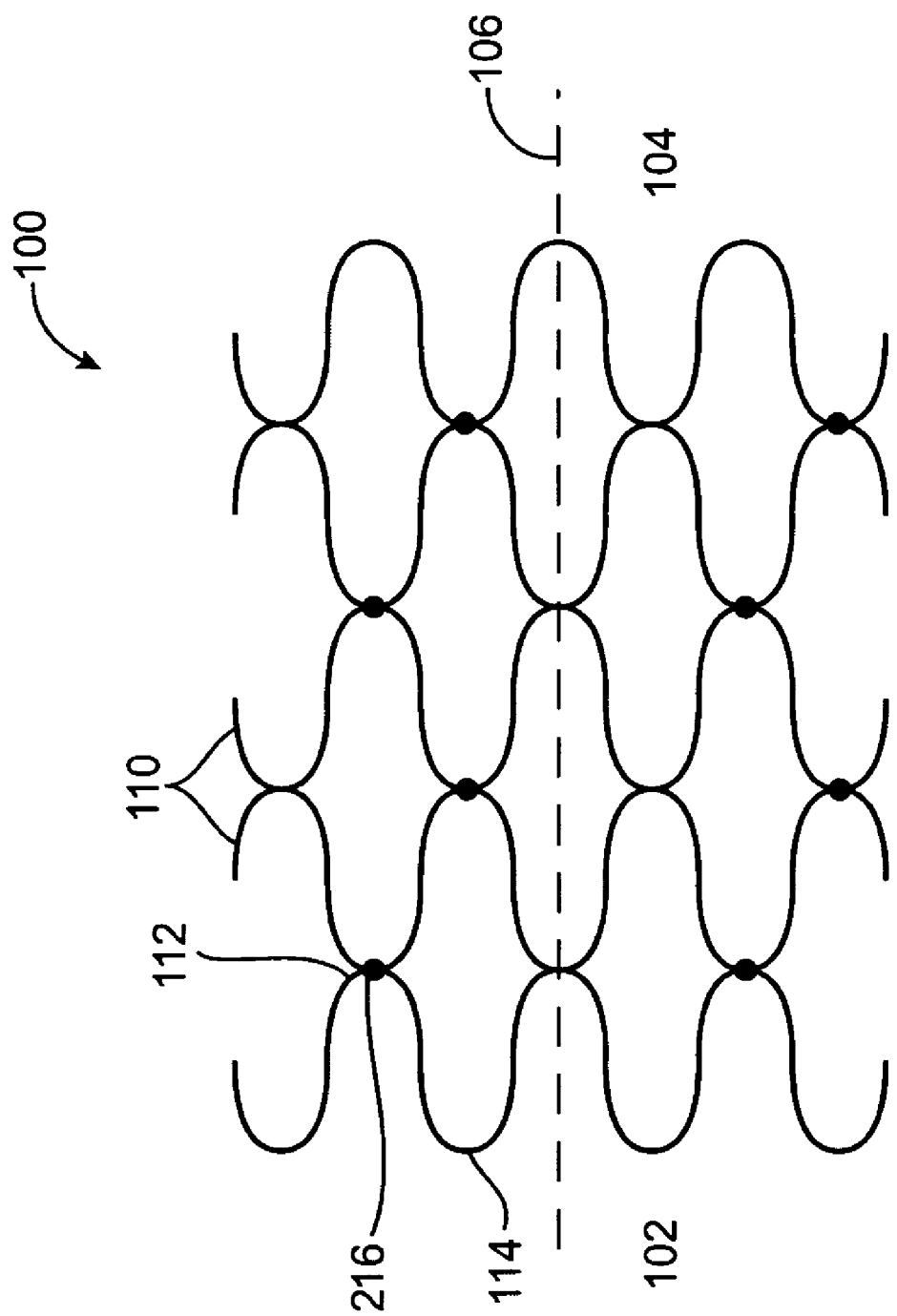
FIG. 2 is a top view of a stent of the present invention, which has been cut and laid open for illustrative purposes

The circumferential rings 110 in the embodiment of FIG. 1 are spaced apart and connected to each other by longitudinal links 118. In the embodiment of FIG. 1, longitudinal links are connected to adjacent circumferential rings 110 at an approximated midpoint between a peak 112 and a valley 114 of each circumferential ring 110. However, it would be understood that the longitudinal links 118 could be attached to each circumferential ring at a peak 112 or a valley 114. Further, it would be understood by one of ordinary skill in the art that the peaks and valleys of adjacent circumferential rings can be lined up such that the adjacent circumferential rings are in-phase with each other, or a peak of one circumferential ring can be aligned with a valley of the adjacent circumferential ring such that adjacent circumferential rings are out-of-phase with each other. Additionally, the number and location of the longitudinal links 118 can be varied. Further, longitudinal links 118 may be excluded altogether, instead directly connecting a peak of one circumferential ring with a valley of an adjacent circumferential ring, for example, through a weld 216, as shown in FIG. 2.

The stent 100 of the present invention is made from iridium. As discussed above, iridium has several properties that are desirable in a stent, such as excellent corrosion resistance, high strength, high modulus, a rapid work-hardening rate, excellent biocompatibility, and high radiopacity. However, iridium in its polycrystalline form is relatively brittle and not suitable for use in a stent unless it is part of an alloy, or modified to produce a "textured" material. A process for texturing polycrystalline iridium in accordance with the present invention provides sufficient ductility for use in a stent, as described above.

An embodiment of a process for texturing polycrystalline iridium such that the crystallographic orientation of the grains are favorably aligned in one direction (for example: in the <110> tensile axis) includes a step of cold/warm working of the polycrystalline iridium at below or just at its re-crystallization temperature, 800-1500° C. depending on prior cold work and processing history. For example, the cold/warm working step could include cold rolling a sheet of polycrystalline iridium under significant load/stress via dies or rollers to break up the original polycrystalline grain structure, at 700-800° C. 700-900° C. is considered "cold" or "warm" working temperature for Ir by those of skill in the art.

The cold/warm working of the material needs to be such that the orientation of rolling favors in alignment of grains in one direction (for example: the <110> direction). Stress/load must be applied such that slip or deformation occurs primarily in one direction. This introduces strain energy into the material, which upon re-crystallization will nucleate new grains with a favorable direction.

Re-crystallization is nucleation of new grains in a material that has been work hardened/plastically deformed and then reheated. Recrystallization of new grains needs to be controlled such that a majority of grains are aligned in the favorable <110> direction. This alignment can be achieved by controlling the amount and direction of strain energy in the material. The amount of strain energy can be controlled by the applied load and/or number of passes through rollers/dies. Working the material needs to occur at or below re-crystallization temperature otherwise it would not work harden.

Another method that can result in favorable orientation is to inhibit the re-crystallization of non-preferred oriented grains by the use of specific, lattice matched second phase particles. Latticed matched second phase particles act as a seed/template such that the metallurgical thermodynamics favor nucleation on certain crystallographic planes or sides of the particle. The second phase particle should have a-b-c spacing similar to the matrix material (Ir) spacing to provide a coherent interface with itself and the matrix material. Examples of suitable second phase particles for use with iridium are Iridium Thorium ($Ir_5$ Th), Ir—Ru, Ir—Ta, Ir—Rh, Ir—V, Ir—Th, Ir—Zr and Ir—W One method of fabricating the stent shown in FIG. 1 is to start with a flat, planar surface of the textured polycrystalline iridium. Flat rings are stamped out of the flat planar surface for the desired number of circumferential rings. The rings are then tumbled to produce a round cross section. The rings are cleaned, and then annealed in a vacuum furnace. The sinusoidal shape is formed in the flat rings to form circumferential rings 110. The circumferential rings 110 are then placed on a mandrel and laser welded together with links 118, alternatively links 118 can be longitudinal links that are in welded to rings 110.

Another method for fabricating stent 100 from a sheet of textured iridium is to begin with a flat sheet of the textured iridium. The shape of the entire stent is then cut out of the flat sheet of textured iridium. This can be accomplished by laser cutting, in which a computer aided design (CAD) drawing of the stent is created. The CAD drawing is then used to generate a machine code, which in turn is used to control a computer numerical control (CNC) laser system. The CNC laser system cuts the shape of the stent directly from the flat sheet of textured iridium, including the sinusoidally shaped circumferential rings and the longitudinal links, if desired. The stent is then rolled and the ends of the flat sheet are welded together, as known in the art. Other methods for etching the stent shape from the flat sheet of texture material can also be used, such a chemical/photolithographic etching.

Alternatively, the flat sheet of texture material can be rolled into a thin-walled hollow cylinder prior to etching. The stent pattern can then be cut directly from the tube, either by laser cutting or chemical/photolithographic etching, as described above. The stent is then appropriately cleaned and polished to be suitable for implantation into the body.

EXAMPLE 1

An example of the texturing method for polycrystalline iridium is described. The method begins with a sheet/bar of polycrystalline iridium, the ductility of which is <3%. In a first step, the sheet/bar of polycrystalline material is rolled between hot dies to achieve a reduction in area of approximately 10% then after the reduction in area step the material is heated above its re-crystallization temperature (approximately 1200° C.). This process is repeated until the desired texturing is achieved. This texturing process results in a sheet of textured iridium with a ductility of >10%.

Using a sheet of textured iridium to make a stent as described above results in stent with higher or equivalent strength, less recoil, more radiopacity, lower crossing profile, better biocompatibility with only ½-⅔ the thickness of current cobalt-chromium or stainless steel stent. For example an iridium stent with 0.0025-0.003 inch thickness will have equivalent properties to a 0.004-0.004 inch thickness steel stent.

While the invention has been particularly shown and described with reference to the preferred embodiments thereof, it will be understood by those skilled in the art that various changes in form and detail may be made there in without departing from the spirit and scope of the invention.

What is claimed is:

1. A method of texturing polycrystalline iridium comprising the steps of:
    cold/warm working of the polycrystalline iridium at equal to or below its re-crystallization temperature to break up the polycrystalline structure such that the orientation favors the <110> direction; and
    re-crystallizing the iridium such that a majority of grains of the polycrystalline iridium are aligned in the <110> direction.

2. The method of claim 1, wherein the step of re-crystallizing the iridium such that the majority of the grains are aligned in the <110> direction is achieved by controlling the amount and direction of strain energy in the material.

3. The method of claim 2, wherein the amount of strain energy is controlled by controlling the applied load and/or number of passes in the cold/warm working step.

4. The method of claim 1, wherein the step of cold/warm working the polycrystalline iridium material is conducted at 700-1100 C.

5. The method of claim 1, wherein rollers or dies are used for the step of cold/warm working of the polycrystalline iridium.

6. The method of claim 1, wherein the step of re-crystallization of the iridium such that the majority of the grains are aligned in the <110> direction is achieved by inhibiting the re-crystallization of non-preferred oriented grains by the use of specific, lattice matched second phase particles.

7. The method of claim 6, wherein the specific, latticed matched second phase particles are selected from the group consisting of $Ir_5$ Iridium Thorium ($Ir_5$ Th), Ir—Ru, Ir—Ta, Ir—Rh, Ir—V, Ir—Th, Ir—Zr and Ir—W.

8. A stent comprising:
    a first circumferential ring; and
    a second circumferential ring coupled to said first circumferential ring;
    wherein said first circumferential ring and said second circumferential ring are made from textured polycrystalline iridium, wherein a majority of grains of the textured polycrystalline iridium are aligned in one direction.

9. The stent of claim 8, further comprising a longitudinal link connecting said first circumferential ring to second main circumferential ring, wherein said longitudinal link is made from textured polycrystalline iridium.

10. A stent comprising:
    a first circumferential ring; and
    a second circumferential ring coupled to said first circumferential ring;
    wherein said first circumferential ring and said second circumferential ring are made from textured polycrystalline iridium, wherein said textured polycrystalline iridium has a ductility exceeding 10%.

11. The stent of claim 8, wherein the majority of grains are aligned in the <110> direction.

* * * * *